US006951714B2

(12) United States Patent
Giovannoni et al.

(10) Patent No.: US 6,951,714 B2
(45) Date of Patent: Oct. 4, 2005

(54) HIGH-THROUGHPUT MICROBIAL CULTURING

(75) Inventors: Stephen Giovannoni, Corvallis, OR (US); Stephanie Connon, Pocatello, ID (US)

(73) Assignee: State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 384 days.

(21) Appl. No.: 10/053,243

(22) Filed: Jan. 16, 2002

(65) Prior Publication Data

US 2002/0164677 A1 Nov. 7, 2002

Related U.S. Application Data

(63) Continuation of application No. 09/675,382, filed on Sep. 29, 2000, now abandoned.
(60) Provisional application No. 60/189,005, filed on Mar. 13, 2000.

(51) Int. Cl.⁷ ............................ C12Q 1/00; C12Q 1/68; C12Q 1/04; C12P 19/34; C07H 21/0204
(52) U.S. Cl. ............................ 435/4; 435/6; 435/34; 435/91.1; 536/23.1; 536/23.7
(58) Field of Search ........................ 435/4, 6, 34, 91.1; 536/23.1, 23.7

(56) References Cited

U.S. PATENT DOCUMENTS

| | | | |
|---|---|---|---|
| 4,427,415 A | 1/1984 | Cleveland | 436/57 |
| 5,756,304 A | 5/1998 | Jovanovich | 435/34 |
| 5,856,175 A | 1/1999 | Thorpe et al. | 435/287.5 |
| 5,861,242 A | 1/1999 | Chee et al. | 435/5 |
| 6,051,380 A | 4/2000 | Sosnowski et al. | 435/6 |

OTHER PUBLICATIONS

Bull et al. (Microbiol. And Molecular Biol. Rev. (2000) 64(3): 573–606).*
Glockner et al. (System. Appl. Microbiol. (1996) 19: 403–406).*
Amann et al. (J. of Bacteriology (1990) 17292): 762–770).*
Button et al., "A Small, Dilute–Cytoplasm, High–Affinity. Novel Bacterium Isolated by Extinction Culture and Having Kinetic Constants Compatible with Growth at Ambient Concentrations of Dissolved Nutrients in Seawater." *App. Environ. Microbiol.*, 64:4467–4476. 1998.
Button. "Nutrient Uptake by Microorganisms according to Kinetic Parameters from Theory as Related to Cytoarchitecture," *Microbio. Mol. Biol. Rev.*, 62:636–645, 1998.
Hoover et al., "Bacteriocins of Lactic Acid," *Academic Press. Inc.*, 23–39, 1993.
Lanoil et al., "Identification of Bacterial Cells by Chromosomal Painting," *Appl. Environ. Microbiol.*, 63:1118–1123, 1997.
Robertson et al., "Determination of the Biomasses of Small Bacteria at Low Concentrations in a Mixture of Species with Forward Light Scatter Measurements by Flow Cytometry," *Appl. Environ. Microbiol.*, 64:3900–3909, 1998.
Wang et al., "A Marine Oligobacterium Harboring Genes Known To Be Part of Aromatic Hydrocarbon Degradation Pathways of Soil Pseudomonads." *Applied and Environmental Microbiology.* 62:2169–2173, 1996.

* cited by examiner

*Primary Examiner*—Jeffrey Fredman
*Assistant Examiner*—Teresa Strzelecka
(74) *Attorney, Agent, or Firm*—Klarquist Sparkman, LLP (57) ABSTRACT

Methods for isolating microbial species, particularly previously uncultured species, from non-laboratory source environments (such as soil, freshwater, seawater, etc.) are disclosed. These methods can include the use of cultures in arrays, and cells deposited on solid surfaces in arrays for detection, and flow cytometry and/or cell sorting and/or dilution cultures.

30 Claims, 2 Drawing Sheets

SEQUENCE LISTING

<160> NUMBER OF SEQ ID NOS: 9

<210> SEQ ID NO 1
<211> LENGTH: 20
<212> TYPE: DNA
<213> ORGANISM: artificial sequence
<220> FEATURE:
<223> OTHER INFORMATION: Synthetic oligonucleotide primer

<400> SEQUENCE: 1
agrgtttgat cmtggctcag                                              20

```
<210> SEQ ID NO 2
<211> LENGTH: 20
<212> TYPE: DNA
<213> ORGANISM: artificial sequence
<220> FEATURE:
<223> OTHER INFORMATION: Synthetic oligonucleotide primer
<221> NAME/KEY: misc_feature
<222> LOCATION: (2)..(2)
<223> OTHER INFORMATION: n = a, t, g, or c
<221> NAME/KEY: misc_feature
<222> LOCATION: (4)..(4)
<223> OTHER INFORMATION: n = a, t, g, or c

<400> SEQUENCE: 2
tnanacatgc aagtcgarcg                                               20

<210> SEQ ID NO 3
<211> LENGTH: 18
<212> TYPE: DNA
<213> ORGANISM: artificial sequence
<220> FEATURE:
<223> OTHER INFORMATION: Synthetic oligonucleotide primer

<400> SEQUENCE: 3
actcctacgg gaggcagc                                                 18

<210> SEQ ID NO 4
<211> LENGTH: 18
<212> TYPE: DNA
<213> ORGANISM: artificial sequence
<220> FEATURE:
<223> OTHER INFORMATION: Synthetic oligonucleotide primer

<400> SEQUENCE: 4
gctgcctccc gtaggagt                                                 18

<210> SEQ ID NO 5
<211> LENGTH: 18
<212> TYPE: DNA
<213> ORGANISM: artificial sequence
<220> FEATURE:
<223> OTHER INFORMATION: Synthetic oligonucleotide primer

<400> SEQUENCE: 5
cagcmgccgc ggtaatwc                                                 18

<210> SEQ ID NO 6
<211> LENGTH: 18
<212> TYPE: DNA
<213> ORGANISM: artificial sequence
<220> FEATURE:
<223> OTHER INFORMATION: Synthetic oligonucleotide primer

<400> SEQUENCE: 6
gwattaccgc ggckgctg                                                 18

<210> SEQ ID NO 7
<211> LENGTH: 15
<212> TYPE: DNA
<213> ORGANISM: artificial sequence
<220> FEATURE:
<223> OTHER INFORMATION: Synthetic oligonucleotide primer

<400> SEQUENCE: 7
acgggcggtg tgtrc                                                    15
```

-continued

```
<210> SEQ ID NO 8
<211> LENGTH: 19
<212> TYPE: DNA
<213> ORGANISM: artificial sequence
<220> FEATURE:
<223> OTHER INFORMATION: Synthetic oligonucleotide primer

<400> SEQUENCE: 8
ggttaccttg ttacgactt                                                    19

<210> SEQ ID NO 9
<211> LENGTH: 20
<212> TYPE: DNA
<213> ORGANISM: artificial sequence
<220> FEATURE:
<223> OTHER INFORMATION: Synthetic oligonucleotide primer
<221> NAME/KEY: misc_feature
<222> LOCATION: (15)..(15)
<223> OTHER INFORMATION: n = a, t, g, or c

<400> SEQUENCE: 9
aaggaggtga tccanccrca                                                   20
```

HIGH-THROUGHPUT MICROBIAL CULTURING

CROSS REFERENCE TO RELATED CASES

This is a continuation of U.S. application Ser. No. 09/675,382, filed on Sep. 29, 2000, now abandoned and claims the benefit of U.S. Provisional Application No. 60/189,005, filed on Mar. 13, 2000, both of which are incorporated herein by reference in their entirety.

ACKNOWLEDGMENT OF GOVERNMENT SUPPORT

This invention was made with government support under National Science Foundation Major Research Instrumentation Grant, No. OIA-9977469. The government has certain rights in this invention.

FIELD

This invention provides methods for the isolation of new species of microbes, and the identification of interactions between microorganisms.

BACKGROUND

Nature contains many microbial species that have never been cultivated. In the past decade researchers have identified microorganisms in nature by direct molecular techniques. These ideas were first formulated by Pace and co-workers, who proposed that natural ecosystems harbored microbial species that were unknown to scientists (Olsen et al., *Ann. Rev. Microbiol.* 40:337–366, 1986; Pace, et al., *Cell* 45:325–326, 1986; Woese, *Microbiol. Rev.* 51:221–271, 1987). By cloning 16S rRNA genes directly from natural ecosystems, it has been possible to catalog a remarkable spectrum of species of unique phylogenetic descent, but for which no laboratory cultures exist (Giovannoni, et al., *Nature* 345:60–63, 1990; Kruske et al. *Appl. Environ. Microbiol.* 63:3614–3621, 1997; Pace, *Science.* 276:734–740, 1997).

The introduction of genetic methods for studying microbial diversity was prompted by the observation that, in many ecosystems, fewer than one cell in one thousand produces a colony on a Petri dish containing nutrient agar—a standard laboratory method of growing heterotrophic bacteria. These observations were dubbed "the great plate count anomaly" (Staley and Konopka, *Ann. Rev. Microbiol.* 39:321–346, 1985). One possible simple explanation for these results is that natural ecosystems harbor microbial species that can not be grown by the standard methods often used by microbiologists.

Techniques for cloning 16S rRNA genes directly from DNA isolated from natural ecosystems circumvented the problem of having to grow microbes to identify them. With this approach it has been possible to catalog from nature a remarkable diversity of prokaryotic species that often represent unique phylogenetic lines of descent, but for which no cultures exist (Barns et al., *Proc. Natl. Acad. Sci USA.* 91:1609–1613, 1994; DeLong *Proc. Natl. Acad. Sci.* 89:5685–5689, 1992; Mullins et al., *Limnol. Oceanogr.* 40:148–158, 1995). These results might well be regarded as a revolution.

Many scientific fields—environmental microbiology, medicine, enzymology, exobiology and genomics—have been impacted by the past decade of discovery of novel, uncultured microbial diversity in the natural world (Pace, *Science.* 276:734–740, 1997; Robertson et al., *SIM News* 46:3–8, 1996).

Molecular studies of in situ microbial diversity are entering a phase of synthesis. Early studies invariably uncovered exciting evidence that ecosystems such as seawater, soil, hot springs and fresh water were populated with novel organisms, prompting numerous laboratories to adopt and apply similar methods. Microbial diversity was viewed by many as a terra incognita, and the spoils were rich new additions to the 16S rRNA gene tree depicting evolutionary themes among cells (Barns et al., *Proc. Natl. Acad. Sci. USA.* 91:1609–1613, 1994). This early phase of discovery led to a phase of synthesis, with the recognition that many of the major unknown gene lineages are widely distributed and therefore are encountered repeatedly in clone libraries prepared by different investigators (Kruske et al., *Appl. Environ. Microbiol.* 63:3614–3621, 1997; Methe et al., *Limnol. Oceanog.* 43:368–374, 1998; Mullins et al., *Limnol. Oceanogr.* 40:148–158, 1995).

Seawater, one of the first ecosystems to be studied by gene cloning, and now the best known, serves as an example to illustrate the very great significance of a few key lineages of organisms. Of 616 bacterial 16S rRNA genes recovered from seawater samples from seven sites, 80% fall into only nine phylogenetic groups. Cultured species are known for only two of these groups (Giovannoni et al., pp. 63–85, In *Evolution of microbial life,* Roberts et al., eds., Cambridge University Press, Cambridge, 1996). This analysis does not include the Group I and Group II marine archaea, because generally their genes are cloned by different methods (DeLong, *Proc. Natl. Acad. Sci.* 89:5685–5689, 1992). Both of these archaeal groups are also uncultured, and their addition raises the number of really abundant marine bacterioplankton groups to ten. Moreover, two of the unique gene lineages first found in seawater were later found also to be abundant in freshwater: the SAR11 lineage of the proteobacteria, and the Group I crenarchaeota.

Similar conclusions are now emerging from studies of freshwater and soils. In one of the best examples, Kruske et al. analyzed soil microbiota from the arid Southwestern United States (*Appl. Environ. Microbiol.* 63:3614–3621, 1997). They observed that five novel clusters of organisms, all having no cultured representatives, accounted for 64% of the genes recovered. More significantly, a thorough survey of data from other studies led to the conclusion that these unknown organisms were widely distributed geographically. Studies of freshwater systems support similar conclusions: lineages such as the SAR11 group, the Acidobacterium group, the Verrucomicrobium group, and the freshwater actinomycete clade, are found in nearly every example examined (Bel'kova et al., *Doklady Biol. Sci.* 348:692–695, 1996; Hioms et al., *Appl. Environ. Microbiol.* 63:2957–2960, 1997; Methe et al., *Limnol. Oceanog.* 43:368–374, 1998; Wise et al., *Appl. Environ. Microbiol.* 63:1505–1514, 1997).

The experimental approach of growing microorganisms from natural systems by dilution of a natural inoculum into media with very low dissolved organic carbon (DOC) concentrations has been described previously, and is considered in a recent review by Schut and colleagues (Schut et al., *Aquat. Microb. Ecol.* 12:177–202, 1997). Despite the success of this approach, it has never been applied to large numbers of cell cultures in small volumes.

There is still a strongly felt need for methods of culturing and identifying novel microorganisms, and for identifying and analyzing positive and negative interactions between microorganisms in culture. It is to these needs that the current invention is addressed.

SUMMARY OF THE DISCLOSURE

Disclosed herein are comprehensive methods useful to bring unknown and uncultured microorganisms—some of the planet's most abundant and elusive species—into culture in scientific laboratories, where their potential as producers of disease, antibiotics, enzymes, as agents of geochemical change, and as key missing links in the evolution of genomes, can be explored.

Certain embodiments provide procedures for miniaturizing the process of culturing cells from varied environments, and high-throughput methods for performing this work.

In specific example disclosed methods, cells are isolated from complex natural communities and deposited into individual compartments, for instance the wells of a microtiter dish or like receptacle. In certain embodiments, the cells are separated such that on average only about one or a few cells are deposited in each compartment, for instance by flow cytometry, cell sorting, or dilution. The individual compartments (e.g., wells of a microtiter dish) contain media suitable for microbial growth, such as sterilized samples of natural waters or other media that may contain added compounds that might support the growth of microorganisms. The growth compartments (e.g., microtiter dishes) are incubated for a time sufficient to allow growth of the cells if such growth is supported by the medium in the compartments, and cell growth is detected and may be quantified. Cell growth can be detected and/or quantified using changes in fluorescence or light scattering, for instance. By way of example, flow cytometry or microscopy can serve as the means of detection of such fluorescence and light-scattering signals.

When direct microscopy is employed as the means of cell detection/quantification, the cells can be first deposited in or on cell microarrays. Such cell microarrays can be created by the use of a cell microarraying procedure, which deposits cells in two-dimensional arrays onto an array substrate, such as a filter of polycarbonate, glass or some other material. Growth of the cultures then can be detected by counting cells in each sector of the array.

Cells can also be identified using cell microarrays, by the hybridization of nucleic acid probes to the cells (for instance, after they are fixed on the original or another array substrate), using probe molecules labeled with a tag, such as a fluorescent tag or other chemical or physical label. Cells alternatively can be identified by a procedure for obtaining gene sequences from very few cells suspended at low densities in an aqueous medium. This gene sequencing procedure can also be used to identify cells that contain specific genes.

Also provided are methods for studying and identifying the interactions, either positive or negative, between two or more different microorganisms (e.g., different strains or different species) in co-culture. Such methods involve placing cells of at least two different microorganisms into a single growth container (e.g., a well of a microtiter plate), and examining the growth characteristics of one or both of the co-cultured microorganisms, to see they are either benefited or detrimented by being grown together. Such methods enable identification of microbes that produce antibiotic compounds, as well as those that produce chemical compounds necessary or beneficial to the culture of another microorganism. Through the miniaturization and automation described herein, such interactions can readily be examined en masse, and statistical analyses performed on the resultant changes in growth kinetics. In certain embodiments, the second microorganism in co-culture with a known or unknown microorganism may be a "reporter" strain, that either inherently bears a reporter function (a detectable physiological or phenotypic change), or that has been engineered (e.g., through transformation) to have such a reporter function. In specific examples, an expression cassette encoding the green fluorescent protein (or like visually detectable molecule) under inducible control is used to detect microorganisms that produce an inducing molecule.

The procedures described herein can be performed manually or can be automated.

The disclosed procedures for high-throughput microbial cultivation and identification collectively overcome existing problems by enabling the culturing of cells and identification of cultures at a higher rate than previously, and/or allowing the detection of cells at the very low cell densities, which might result from a low growth rate or other limitations to cell growth, and/or by permitting the miniaturization and/or automation of these procedures.

SEQUENCE LISTING

The nucleic and/or amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown. In the accompanying sequence listing:

SEQ ID NOs 1–9: show eubacterial and/or universal small subunit rRNA primers. SEQ ID NOs: 1–3 and 5 are all forward (upstream) primers; SEQ ID NOs: 4 and 6–9 are reverse (downstream) primers.

DETAILED DESCRIPTION

I. Abbreviations

BCP: bacterial chromosome painting
DOC: dissolved organic carbon
FISH: fluorescence in situ hybridization
GFP: green fluorescent protein
HTS: high throughput screening II. Definitions Unless otherwise defined, all technical and scientific terms used herein have the same meaning as commonly understood by one of ordinary skill in the art to which this invention belongs. Definitions of common terms in molecular biology may be found, for instance, in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference,* published by VCH Publishers, Inc., 1995 (ISBN 1-56081-569-8).

In order to facilitate review of the various embodiments of the invention, definitions of specific terms are provided throughout the text as needed. The singular terms "a", "an", and "the" include plural referents unless context clearly indicates otherwise.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

III. High-Throughput Culturing of Novel Organisms

The following hypotheses may explain why many microorganisms are difficult to cultivate in the laboratory:

1) they can only grow in narrowly defined conditions that are not likely to be created by chance experimentation;
2) they grow slowly, or at best achieve low cell densities in culture, and therefore growth is not detected; and/or
3) they require interactions with other organisms in consortia.

The high-throughput culturing methods described here overcome these problems because 1) they can detect populations of at least $10^3$ cells/ml originating from a single cell; 2) they enable the detection of the low cell numbers that would be found when cells are grown on environmentally realistic concentrations of DOC (10 $\mu$g/L–5 mg/L), and also would make it tractable to study species that grow very slowly or to low cell densities, even when cultured at higher nutrient concentrations, 3) they can be used to systematically test random combinations of cells with large enough numbers of replicates to identify combinations that can only grow as consortia (a set of different cells that interact synergistically); and 4) the high rate of culture replication provided by these procedures can be used to systematically explore variations in the chemical composition and physical conditions used to grow cells.

The methods disclosed herein are designed to interface with robotics and the miniaturization of organism cultivation in microtiter dishes. In brief overview (see FIGS. 1 and 2), culture analysis begins with the transport, either by robotics or by hand, of cell cultures from microtiter dishes to a micro-filtration manifold (e.g., similar to a dot-blot apparatus such as those described in U.S. Pat. No. 4,427,415), for instance one of custom design. The wells of the filtration manifold for instance may be 3 mm in diameter, and arrayed to fit on the surface of a glass microscope slide. Other arrangements and well sizes are also envisioned.

Figure 1:
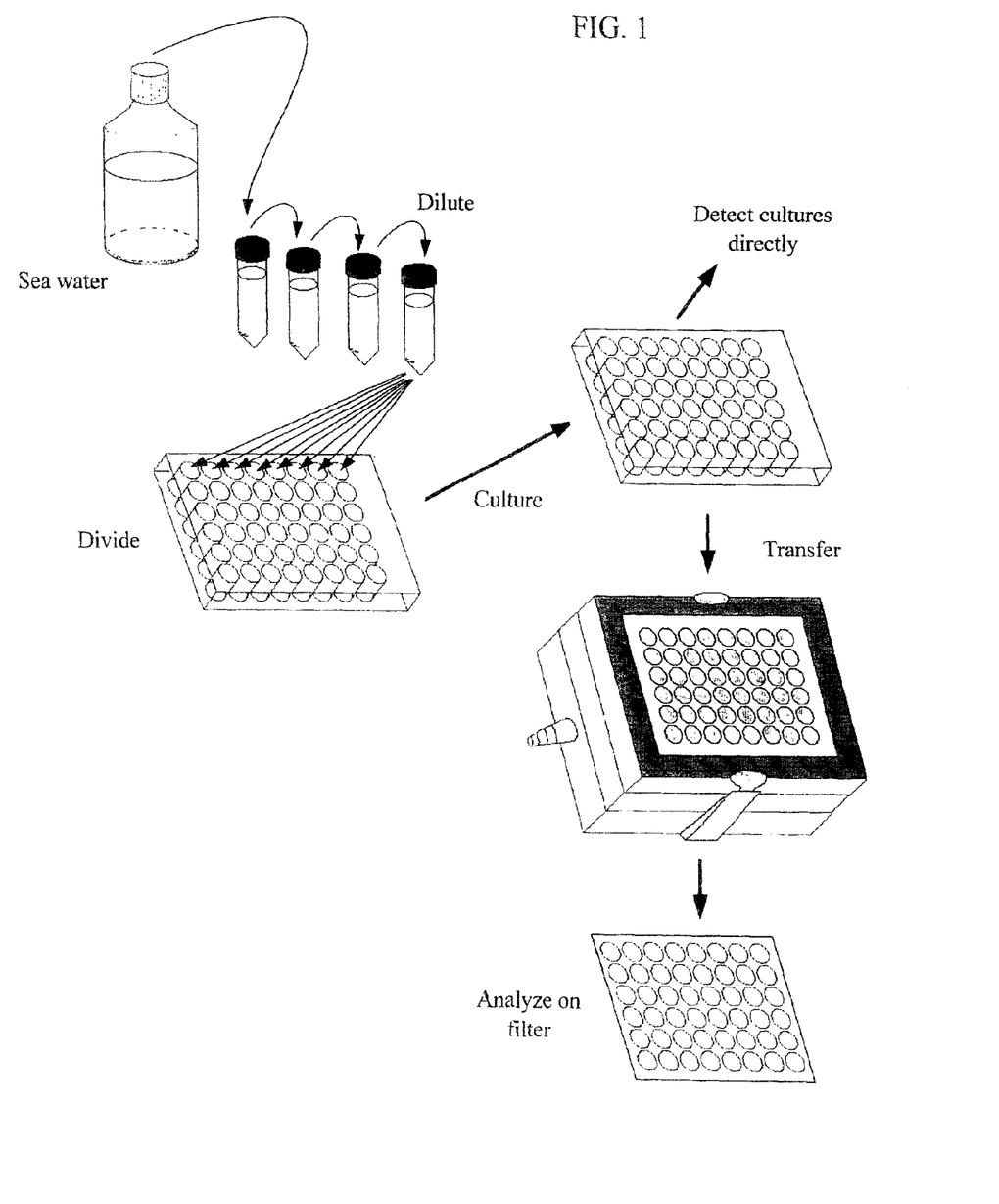
FIG. 1 is a block diagram overview of one embodiment of the microbial culturing and identification techniques described herein.
Figure 2:
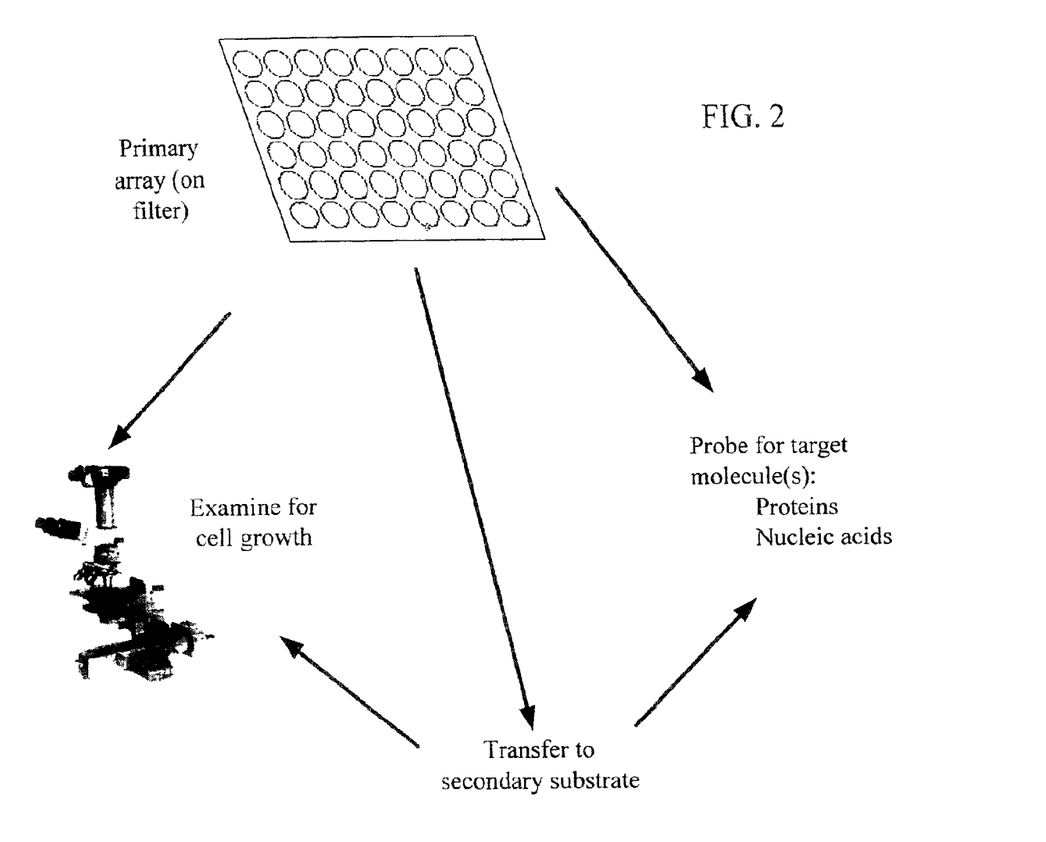
FIG. 2 shows a schematic overview of methods for analysis and identification of cells arrayed as described herein.

The cells are collected on polycarbonate or other filter membranes and may optionally be transferred to the glass slides. Such slides may optionally be coated so as to encourage the transfer of cells from the membrane. In certain embodiments, fixation, dehydration of the cells, and nucleic acid hybridizations occur with cells attached to glass slides. The primary filtration membrane (e.g., a polycarbonate membrane) can be used directly for hybridization with fluorescent nucleic acid probes, staining with DAPI, and/or direct scanning by microscopy as an alternative or additional system for examining the cells.

IV. Sources of Cells

The methods described herein are suitable for isolating, culturing, identifying, and studying microbes from any environment, in particular natural (e.g., non-laboratory) environments in which individual species or strains of microbes are generally found at relatively low concentrations. Such environments include, for instance, oceans or other bodies of water, including freshwater lakes and ponds, rivers, streams, saline lakes, and ground water aquifers; non-aquatic terrestrial environments, including soils, industrial sites, and man-made structures, and biological specimens, such as on, in, or in association with animals or plants, including decaying animals or plants.

"Extreme" environments may also serve as sources for organisms that are cultured or isolated using the described techniques; such extreme environments include regions of high temperature (e.g., inside or near volcanoes, at lava or steam vents, at under-water lava sites, in hot-springs, or at certain heated industrial sites), low temperature (e.g., near the Poles, or in freezers or cold storage units), salinity extremes (e.g., certain natural salt springs, drying seas, or at pollution sites), and so forth. In addition, the techniques described can be used to rapidly and effectively isolate, culture, and categorize microorganisms found in truly novel environments, including on other planets, moons, or on space debris.

V. High-Throughput Culturing

Procedures for obtaining cultures of cells using culture arrays are disclosed. These procedures can be used to discover new microbial organisms that have not been amenable to standard culturing techniques, or combinations of cell types (e.g., different species or different strains) that may require each other's presence to replicate in culture. The described methods can be used to culture microbial cells at substrate carbon concentrations and cell densities that are 1000-fold lower than standard laboratory conditions.

The integration of a flow cytometer to separate cells, with robotic automation to accelerate the processing of samples, permits the screening of large arrays of cultures, and thereby makes it possible to screen a large number of variables (e.g., culturing variables) and replicates. This makes it feasible to identify chemical and physical conditions that permit the growth of environmentally significant (but usually not previously culturable) microorganisms, and to optimize these conditions. The design of this system also enables production of data on the probabilities of culturing cells, and on their growth rates at cell densities and substrate concentrations that are more reflective of their native situation, but that have remained difficult to study by other means.

VI. Culturing conditions

An important factor in the success of the procedures described herein is their suitability for use with natural organic carbon and other compounds found in nature as sources of nutrients for microbial growth. However, these procedures can also be used to study microbial growth on purified chemical compounds. Examples of growth medium variables that can be used in various combinations to provide different media for growth of microorganisms as described herein:

1) natural waters from different sources;
2) organic compounds, including hydrocarbons, amino acids, sugars, organic acids such as Krebs cycle intermediates, vitamins, and polymeric compounds such as sugar polymers, proteins, and nucleic acids;
3) inorganic nutrients, often referred to as "trace" nutrients, such as Cu, Va, Mo, Fe, Zn, Co, Mn, B, P, N, Ni; and
4) physical variables, such as temperature, osmotic strength of the medium, agitation, gravity, atmospheric pressure, pH and light intensity.

Each of these variables can be changed independently, and the high-throughput nature of the methods described enables myriad combinations to be analyzed with minimal time and resource investment.

In certain embodiments, cells can also be cultured on conventional growth media, to compare growth rates, culturability, or like parameters. For instance, a sample of the raw source material may be used as a starting culture for growth on nutrient agar plates. In other instances, a portion of some or all of the microbial cultures that show growth in the micro-culture compartments (e.g., the compartments of a microtiter dish) can be used to inoculate traditional medium (either liquid medium or nutrient agar plates, for instance), in order to examine whether the microbes will grow under traditional conditions.

VII. Arrays

One particular improvement that is exhibited by certain disclosed embodiments is the use of "arrays" of cells or cell samples, which are placed on an array substrate such as a primary filter substrate or a secondary array substrate (e.g., a glass slide to which cells are transferred).

Arrays, as the term is used herein, are arrangements of addressable locations on a substrate; each address may contain a sample of one or more types of microbial cells. A "microarray" is an array that is miniaturized so as to require microscopic examination for evaluation of hybridization or other detection signals. "Macroarrays" are some what larger, such that at least the spot at each address is recognizable by the naked human eye; in some embodiments, a hybridization or other detection signal (for instance, a signal used to identify a specific cell type) is also detectable without additional magnification on a macroarray. Primary examination for the presence of cells on the array is usually carried out using a microscope or other magnifying device.

The use of the term "array" here is unlike that involved in DNA microchip technology, because the target nucleic acids (DNA and/or RNA) is physically restrained (immobilized) inside of microbial cells (which may be fixed on the array), while a (usually labeled) "probe" is applied in solution, for instance to detect the presence of a particular nucleic acid molecule within one of the cells on the array. In standard DNA microchip technology the converse is seen—target DNA (in solution) is labeled, and the "probe" (identified individual nucleic acid molecules) is immobilized on the array.

Within an array, each arrayed cell sample or mixture of cells is addressable, in that its location can be reliably and consistently determined within the at least the two dimensions of the array surface. Thus, in ordered arrays the location of each cell sample is assigned to the sample at the time when it is spotted onto the array surface and usually a key is provided in order to correlate each location with the appropriate "target" cell sample. Often, ordered arrays are arranged in a symmetrical grid pattern, but samples could be arranged in other patterns (e.g., in radially distributed lines or ordered clusters).

The shape of the cell sample application "spot" is immaterial to the invention. Thus, though the term "spot" is used throughout this specification, it refers generally to a localized deposit of cells, and is not limited to a round or substantially round region. For instance, essentially square regions of cell sample application can be used with arrays of this invention, as can be regions that are essentially rectangular (such as slot blot application), or triangular, oval, or irregular. The shape of the array itself is also immaterial to the invention, though it is usually substantially flat and may be rectangular or square in general shape.

Microbial arrays as used with this invention may vary significantly in their structure, composition, and intended functionality. The high throughput microbial isolation/identification system is amenable to use in either a macroarray or a microarray format, or a combination thereof. Such arrays can include, for example, at least 20, at least 50, at least 100, at least 150, at least 200, at least 500, at least 1000, or at least 5000 or more array elements (such as spots). In the case of macro-arrays, no additional sophisticated equipment is usually required to detect a bound probe (e.g., a hybridization probe) on the array, though quantification may be assisted by known automated scanning and/or quantification techniques and equipment. Thus, macro-array analysis as described herein can be carried out in most research laboratories and biotechnology companies, without the need for investment in specialized and expensive reading equipment. Of course, examination of the microbes themselves on an array surface will often involve enlargement equipment, such as a microscope (e.g., a light or fluorescent microscope, or an electron microscope).

Examples of substrates for the microbial arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (e.g., glass or a supported membrane) or flexible (such as a polymer membrane). One commercially available microarray system that can be used with the arrays of this invention is the FAST™ slides system (Schleicher & Schuell, Dassel, Germany), which system incorporates a patch of polymer on the surface of a glass slide.

In general, a target on the array should be discrete, in that signals (e.g., hybridization signals) from that target can be distinguished from signals of neighboring targets, either by the naked eye (macroarrays) or by scanning or reading by a piece of equipment or with the assistance of a microscope (microarrays). Detection of the microbes themselves, such as on primary or secondary growth identification arrays, is generally carried out using a microscope whether the array is a micro- or macroarray.

Microbial arrays of the invention are often arrayed on polymer membranes, either supported or not, and can be of any size, but typically will be greater than a square centimeter. Other examples of array substrates include glass, fiber, plastic and metal. Spot arrangement on the array is such that individual spots can be distinguished from each other when the sample is read; typically, the diameter of the spot is about equal to the spacing between individual dots.

Sample spots on macroarrays are of a relatively large size, for instance large enough to permit detection of a hybridization signal without the assistance of a microscope or other sophisticated enlargement equipment. Thus, spots may be as small as about 0.1 mm across, with a separation of about the same distance, and can be larger. Larger sample spots on macroarrays, for example, may be about 0.5, 1, 2, 3, 5, 7, or 10 mm across. Even larger spots may be larger than 10 mm (1 cm) across, in certain specific embodiments. The array size will in general be correlated the size of the sample spots applied to the array, in that larger spots will usually be found on larger arrays, while smaller spots may be found on smaller arrays. This correlation is not necessary to the invention, though.

In microarray formats of the disclosed microbial arrays, a common feature is the small size of the target array, for example on the order of a squared centimeter or less. A squared centimeter (1 cm by 1 cm) is large enough to contain over 2,500 individual target spots, if each spot has a diameter of 0.1 mm and spots are separated by 0.1 mm from each other. The power of microarray-format resides not only in the number of different microorganisms that can be probed simultaneously, but also in how few cells are needed for the target.

In addition, the surface area of sample application for each "spot" will influence how densely the sample microorganisms are immobilized on the array surface. Thus, a larger spot (having a greater surface area) will generally display microorganisms at a relatively lower density than a smaller sample spot (having a smaller surface area).

Another way to describe an array is its density—the number of samples in a certain specified surface area. For macroarrays of the current invention, array density may be between about one target per squared decimeter (or one target address in a 10 cm by 10 cm region of the array substrate) to about 50 targets per squared centimeter (50 targets within a 1 cm by 1 cm region of the substrate). For microarrays, array density will usually be one target per squared centimeter or more, for instance about 50, about 100, about 200, about 300, about 400, about 500, about 1000, about 1500, about 2,500, about 5,000, about 10,000, or more targets per squared centimeter.

VIII. Detecting Cell Growth/Replication

It is necessary to detect whether cells replicate and grow in the medium provided, while at the same time preserving at least a portion of the culture for further examination and perpetuation. Thus, usually only a portion of each individual culture is used for detecting the presence (or absence) of cell growth.

Any method that can deposit a portion of the cell culture onto a surface can be used to detect cell growth from cultured samples. In certain embodiments, it is beneficial to use a method that allows the removal of some or substantially all of the culture medium from the culture sample, and thereby leaves the cells relatively fluid-free on a surface appropriate for analysis (e.g., the surface of an array material). One such method is by allowing the culture sample to flow within a defined channel onto a predefined region(s) of the array substrate. Typical "flow channel" application methods for applying the polypeptides to arrays of the present invention are represented by dot-blot or slot-blot systems (see, e.g., U.S. Pat. Nos. 4,427,415 and 5,283,039).

An alternative method for applying cell cultures to an array substrate is "spotting" the cell culture on predefined regions (each corresponding to an array address). In a spotting technique, the target cells are delivered by directly depositing (rather than flowing) relatively small quantities of them in selected regions. For instance, a dispenser can move from address to address, depositing only as much target as necessary at each stop. Such techniques usually apply only a very small volume of liquid at each site, and may be inappropriate for dilute cultures unless the cultures are first concentrated. Typical dispensers include an ink-jet printer or a micropipette to deliver the target in solution to the substrate and a robotic system to control the position of the micropipette with respect to the substrate. In other embodiments, the dispenser includes a series of tubes, a manifold, an array of pipettes, or the like so that the target cell culture samples can be delivered to the array addresses simultaneously.

In certain embodiments, it is advantageous to determine the growth (or non-growth) of micro-cultured samples by scanning the cultures (e.g., in microtiter plates) directly. Such scanning can include, for instance, determination of the optical density (OD) of each individual cell culture; the optical density is directly related to the number of cells in the sample, though the relationship may be different for different cell types and culturing conditions. Such scanning for OD can be automated.

IX. High Throughput Screening of Dilute Cultures

In general, for the screening and identification of dilute cell cultures, the arraying and application techniques discussed above are applicable.

In certain embodiments of this invention, the high-throughput cell screening system can be used to identify cells that are either 1) phylogenetically unique, or 2) that display particularly physiological properties, or possess particular genetic information. Arrays of cells are constructed and used to identify the cells by their DNA or ribosomal RNA signatures or by expression of a certain protein or epitope (see below). The DNA sequence of genes in single cells can be determined by reacting the cells with fluorescent (or otherwise labeled) nucleic acid probes and visualizing the cells using an automated laser scanning microscope or other device suitable for scanning an array.

In the disclosed systems, labeled (e.g., with a fluorescent tag) DNA probes can be either phylogenetic or functional. For example, heterologous probes for genes involved in polyketide synthesis (see, e.g., WO 98/58085) can be used to screen microbial isolates for genes in these functional gene classes.

High throughput screening (HTS) technology can be employed in at least two modes: "weed" mode, to rapidly eliminate common microbial species, and "target" mode, to identify key target species (for example, members of the SAR11 group). In addition to detecting hybridization, the HTS approaches provide statistical information on cell numbers and size. Positive wells that hybridize neither to "weed" or "target" probe suites likely represent growth of novel organisms, which can be identified through, for instance, 16S rRNA gene sequencing (see below).

Fluid cytometry is useful for detecting small prokaryotic cells by light scattering and generalized DNA fluorescence techniques, but it is not suitable for the identification of small cells by FISH techniques, because the microsecond duration time of the fluorescence detection event imposes a relatively low sensitivity to fluorescence signals. With direct microscopy, exposures can be integrated over periods thousands of times longer, thereby providing more sensitive detection.

The use of arrays with the disclosed system permits the culturing and analysis of large numbers of organisms in parallel. For instance, at least 20, at least 50, at least 100, at least 400, at least 500, at least 1000, at least 1500, or more cultures can be incubated and analyzed in a single process. In certain embodiments, even more cultures, such as 2000 or more, are processed at the same time. Processing of such large numbers of samples is further facilitated by automating some or all of the process, such as sample dilution and distribution into microtiter plate compartments, culturing processes, sampling and primary detection of cell growth (e.g., by arraying samples of each culture onto membranes or glass slides and detecting the growth of cells), and microorganism detection and identification (e.g., using techniques described herein).

X. Identification of Organisms

Once organisms have been isolated and cultured by the methods described herein, it is beneficial to identify them. Such identification can be cursory (i.e., as brief as "has this been isolated before" versus "is it new") through a continuous spectrum to very detailed (what is this organism, how does it relate phylogenetically to known organisms, and what is it good or bad for). Organism identification can therefore involve up to several different levels of analysis, and each analysis can be based on a different characteristic of the organism. Such analyses can include nucleic acid analysis (e.g., analysis of individual specific genes, either as to their presence or their exact sequence, or expression of a particular gene or a family of genes), protein analysis (e.g., at a functional level using direct or indirect enzyme assays, or at a structural level using immuno-detection techniques), and so forth.

Prior to carrying out intensive molecular analysis of isolated cultures, it may be useful to confirm that the culture arose from a single cell, and is therefore a pure culture (except where, as discussed below, organisms are intentionally mixed). Organisms can often be distinguished based on direct microscopic analysis (do all of the cells in a sample look the same on examination), staining characteristics, simple molecular analysis (such as a simply restriction fragment length polymorphism (RFLP) determination), and so forth. In certain embodiments of the invention, however, it is not absolutely necessary to perform this purity confirmation step, as mixed cultures will be apparent in subsequent analysis.

A. Nucleic Acid Analysis

1. Amplification of a Specific Sequence

Methods provided for identifying microorganisms according to the invention include amplifying and sequencing genes from very small numbers of cells in dilute suspensions. The provided procedures overcome the problems of concentrating cells and their DNA from dilute suspension when very small numbers of cells are available. The provided procedures can be used to identify cells by gene sequence or to identify cells that have particular genes or gene families, for instance with a functional significance.

As used herein, the phrase "nucleic acid amplification" refers to techniques that increases the number of copies of a nucleic acid molecule in a sample or specimen. An example of nucleic acid amplification is the polymerase chain reaction (PCR), in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid.

Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

In addition to the illustrative example primers provided herein, primers have also been designed, and new ones are continually being designed, for individual species or phylogenetic groups of microorganisms. Such narrowly targeted primers can be used with the methods described herein to screen specifically only the microorganisms of interest.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of an rRNA-encoding nucleotide or flanking region thereof will anneal to a target sequence with a higher specificity than a corresponding primer of only 15 nucleotides. Thus, in order to obtain greater specificity, probes and primers can be selected that comprise at least 20, 25, 30, 35, 40, 45, 50 or more consecutive nucleotides of a target nucleotide sequence such as the 16S rRNA.

Common techniques for the preparation of DNA extracts for nucleic acid amplification (e.g., PCR) include phenol/chloroform extraction or use of one of the many DNA extraction kits that are available on the market. All of these procedures loses much of the DNA during preparation/purification. It is difficult to obtain gene amplification from as few as 20 cells using these DNA purification methods. Another way that DNA can be amplified is by adding cells directly to the nucleic acid amplification reaction mix and relying on the denaturation step of the amplification to lyse the cells and release the DNA. However, cells often do not lyse by this method and the culture medium can inhibit the reaction.

Described herein is a process to identify cells by gene sequencing from as few as about 20 cells that are in ca. milliliter volumes of medium. First the cells are concentrated by use of a commercial 10,000 molecular weight ultrafiltration membrane in a centrifugation concentrator. Then lysis buffer is added to the concentrator and allowed to sit for some time, for instance about 5 minutes, about 15 minutes, about 30 minutes, about 60 minutes, about 120 minutes, or more. The lysis buffer is then rinsed with three rinses of water and the cell material is collected from the concentrator. An initial 20 µl PCR reaction can be done using liquid collected from the concentrator and a second 60–100 µl PCR is done using 1 µl from the previous PCR for a total of 50–66 cycles of PCR. For the PCR positive controls, a dilution series of the DNA gene of interest is needed. For instance, $10^8$, 2000, 200, 100 and 20 copies of the 16S DNA gene can be used as positive controls, which show very consistent and concentrated PCR product from as few as 20 copies.

The use of UV irradiation to eliminate DNA contamination from reagents and other supplies (such as tubes, tips, and concentrator columns) is essential to the disclosed processes of analyzing nucleic acids from dilute cultures. All dry tubes are irradiated for 5–7 minutes. All liquid reagents are irradiated in a sealed polypropylene micro-centrifuge style tube for 3–5 minutes. If too much irradiation is used, the PCR fails; if too little UV is used then the DNA contamination that is in all reagents and tubes will amplify in the negative control.

The product of nucleic acid amplification reactions may be characterized by electrophoresis, restriction endonuclease cleavage patterns, oligonucleotide hybridization or ligation, and/or nucleic acid sequencing, using standard techniques.

2. Fluorescent Labeling of Nucleic Acids

Fluorescence in situ hybridization (FISH) using DNA oligomers homologous or complementary to the RNA sequences in ribosomes of fixed, intact cells is now used widely in microbiology for cell identification (Amann et al., *Microbiol. Rev.* 59:143–169, 1995; Amann et al, *J. Bacteriol.* 172:762–770, 1990; DeLong et al., *Science.* 243:1360–1363, 1989; Giovannoni et al., *J. Bacteriol.* 170:720–726, 1988). More recently, a second technique, called bacterial chromosomal painting (BCP), was introduced for cell identification (Lanoil & Giovannoni, *Appl. Environ. Microb.,* 63:1118–1123, 1997). While FISH is based on the design of probes from computer databases, BCP uses longer, cloned DNA probes. BCP can be used to detect quiescent cells and impermeable cells, or to localize functional genomic DNA regions inside of cells.

Both of these methods (FISH and BCP) can be used to detect and count cells according to methods of this invention. Both of these techniques can be multiplexed, that is, the hybridization of multiple probes to arrays of cells can be detected by the simultaneous scanning of samples at multiple wavelengths.

BCP has the potential to detect cells with specific metabolic functions by screening them for the presence of functional DNA domains. For example, it is possible to detect cells harboring genes for antibiotic biosynthetic pathways or pathways for the degradation of xenobiotic compounds even when cell suspensions are too dilute or "delicate" for typical (traditional) microbiological assays to function.

B. Protein Analysis

In addition to analysis of nucleic acids, organisms cultured using the disclosed techniques can be characterized and identified based on the presence (or absence) of proteins directly. Such analysis can be based on the activity of the specified protein, e.g., through an enzyme assay or by the response of a co-cultured organisms, or by the mere presence of the specified protein (which can for instance be determined using immunologic methods, such as in situ immunofluorescent antibody staining.

1. Enzyme Assays

By way of example, fluorescent (fluorgenic) substrate analogs can be pipetted into cultures (e.g., microtiter plate cultures), followed by incubation and screening for reaction products, thereby identifying cultures on a basis of their enzymatic activities.

Fluorogenic substrates are compounds that form fluorescent products when cleaved by specific enzymes. They are useful for detecting enzymatic activities. For instance, the enzyme alkaline phosphatase dephosphorylates the fluorogenic substrate ELF-97 (fluorescein diphosphate, Molecular Probes) to form a bright, yellow-green fluorescent precipitate, ELF-97 alcohol. Alkaline phosphatase activity is associated with phosphorus starvation in some bacteria and phytoplankton. (Huang et al, *Appl. Environ. Microbiol.* 64:1526–1531, 1998; Dyhrrnan and Palenik, *Appl. Environ. Microbiol.* 65:3205–3212, 1999).

2. Co-Cultivation Response

Additionally, the activity of an enzyme carried by a microbial isolate can be assayed based on the response (or degree of response) of a co-cultured organism (such as a reporter organism). A more detailed discussion of such methods is provided below.

3. Immunological Techniques

Methods are also provided herein for detecting and/or identifying microorganisms isolated from a source environment by binding at least one antibody or antibody-derived molecule to a molecule, or more particularly an epitope of a molecule, of the microorganism.

Anti-microorganism protein antibodies may be produced using standard procedures described in a number of texts, including Harlow and Lane (*Antibodies, A Laboratory Manual,* CSHL, New York, 1988). The determination that a particular agent binds substantially only to a protein of the desired microorganism may readily be made by using or adapting routine procedures. One suitable in vitro assay makes use of the Western blotting procedure (described in many standard texts, including Harlow and Lane (*Antibodies, A Laboratory Manual,* CSHL, New York, 1988)).

Shorter fragments of antibodies (antibody-derived molecules, for instance, FAbs, Fvs, and single-chain Fvs (SCFvs)) can also serve as specific binding agents. Methods of making these fragments are routine.

Detection of antibodies that bind to cells on an array of this invention can be carried out using standard techniques, for instance ELISA assays that provide a detectable signal, for instance a fluorescent or luminescent signal.

XI. Detection of Interactions Between Cells in Culture

Methods provided herein also can be used to identify positive and/or negative interactions between microbial cells, such as those caused by the production of antimicrobial compounds, quorum-sensing compounds, or syntrophic relationships, i.e., those involving the transfer of metabolites between cells of different species. This invention makes use of high throughput culturing methods in which cells are grown in microtiter dish arrays and identified by high throughput techniques. Deposition of multiple cells into each culture well and subsequent detection and identification of cultured cells statistical data will reveal patterns of positive and negative interactions between cells of different types or species. This procedure might include the sorting or dilution of cells from natural systems into culture wells (arrays) or the use of combinations of microbial cells from natural systems with pure cultures of cells. To illustrate, combinations of cell types that were never seen growing in co-culture despite information showing that these cells could grow axenically in the system would indicate negative interactions between these two cell types, whereas two cell types only growing in co-culture and never axenically would suggest a positive interaction, such as a syntrophic or other consortial relationship.

Methods of invention also can be used to systematically search for interactions between cultures of cells from nature and reporter strains of microorganisms, for example for the purpose of detecting antibiotic production by a novel bacterial strain. For example, reporter strains of bacteria, which produce green fluorescent protein (GFP) or another "marker" compound that is readily detectable and/or quantifiable, could be distributed into the wells of microtiter dishes, with unknown cells from nature, such that the interference (or synergism) of the unknown cells with the growth of the reporter strains would be easily detected. Similarly, reporter strains engineered to produce GFP in response to a particular compound, could be used in the HTC format to search for cultures of unknown cells from nature that produce the compound in question.

Embodiments thus include methods wherein a cultured strain of microorganism, called a reporter strain, is added to the medium with an unknown cell from nature, such that production of at least one compound by the unknown cell is revealed by a growth or genetic responses of the reporter strain.

XII. Computer Assisted (Automated) Detection and Analysis

The data generated using a microbial array according to this invention (e.g., growth patterns, growth interaction patterns, and/or hybridization signals) can be analyzed using computerized systems. For instance, the array can be read by a computerized "reader" or scanner and the quantification of the binding of probe to individual addresses on the array carried out using computer algorithms. Similarly, a reader can be used to detect the presence (or absence) of cell growth in cultures that have been arrayed. Such analysis of the array can be referred to as "automated detection" in that the data is being gathered by an automated reader system.

In the case of labels (e.g., hybridization labels) that emit detectable electromagnetic waves or particles, the emitted light (e.g., fluorescence or luminescence) or radioactivity can be detected by sensitive cameras, confocal scanners, image analysis devices, radioactive film or a Phosphoimager, which capture the signals (such as a color image) from the array. A computer with image analysis software then detects this image, and analyzes the intensity of the signal for each cell sample location (address) in the array. Signals can be compared between spots on a single array, or between arrays (such as a single array that is sequentially probed with multiple different probe molecules).

Computer algorithms can also be used for comparison between spots on a single array or on multiple arrays. In addition, the data from an array can be stored in a computer readable form.

Certain examples of automated array readers (scanners) will be controlled by a computer and software programmed to direct the individual components of the reader (e.g., mechanical components such as motors, analysis components such as signal interpretation and background subtraction). Optionally software may also be provided to control a graphic user interface and one or more systems for sorting, categorizing, storing, analyzing, or otherwise processing the data output of the reader.

By way of example, to "read" an array according to this invention that has been assayed with a detectable probe to produce binding (e.g., a binding pattern), the array can be placed into (or onto, or below, etc., depending on the location of the detector system) the reader and a detectable signal indicative of probe binding detected by the reader. Those addresses at which the probe has bound to immobilized polypeptide sample provide a detectable signal, e.g., in the form of electromagnetic radiation. These detectable signals could be associated with an address identifier signal, identifying the site of the complex. The reader gathers information from each of the addresses, associates it with the address identifier signal, and recognizes addresses with a detectable signal as distinct from those not producing such a signal. Certain readers are also capable of detecting intermediate levels of signal, between no signal at all and a high signal, such that quantification of signals at individual addresses is enabled.

Certain readers that can be used to collect data from the arrays of this invention, especially those that have been probed using a fluorescently tagged molecule, will include a light source for optical radiation emission. The wavelength of the excitation light will usually be in the UV or visible range, but in some situations may be extended into the infra-red range. A beam splitter can direct the reader-emitted excitation beam into the object lens, which for instance may be mounted such that it can move in the x, y and z directions in relation to the surface of the array substrate. The objective lens focuses the excitation light onto the array, and more particularly onto the (microbial cell) targets on the array. Light at longer wavelengths than the excitation light is emitted from addresses on the array that contain fluorescently-labeled probe molecules (i.e., those addresses containing a cell to which the probe binds).

In certain embodiments of the invention, the array may be movably disposed within the reader as it is being read, such that the array itself moves (for instance, rotates) while the reader detects information from each address. Alternatively, the array may be stationary within the reader while the reader detection system moves across or above or around the array to detect information from the addresses of the array. Specific movable-format array readers are known and described, for instance in U.S. Pat. No. 5,922,617, hereby incorporated in its entirety by reference. Examples of methods for generating optical data storage focusing and tracking signals are also known (see, for example, U.S. Pat. No. 5,461,599).

The invention is illustrated by the following non-limiting Examples.

EXAMPLES

Example 1

Collection of Samples from Seawater

Samples of Oregon coastal seawater were taken from the following locations: collected from the jetty in Newport, Oreg.; and collected from a vessel within fifteen miles of the entrance of Newport, Oreg. Samples were preserved prior to culturing by maintaining them at the same temperature as the environment from which they were collected, or a colder temperature. Samples were diluted into microtiter dishes as soon as was feasible in all cases.

Example 2

Dilution of Cells into Microtiter Plates

Cells were DAPI stained and counted using standard fluorescence microscopy to get a count of cells per ml of the original sample. Based upon this calculation, a dilution was made using the desired culture medium (see below) for a final starting culture density of 1 to 10 cells per ml, depending on the application. The dilution was pipetted as 1 ml volumes into non-tissue treated 48-well microtiter plates using a multi-channel pipettor (Labsystems Finnpipette).

Example 3

Culturing of Microorganisms

Microtiter plates filled as discussed above were sealed with Parafilm™ to prevent evaporation, and placed in a controlled temperature incubator at 15° C. The cultures were incubated for three weeks in order to permit growth of the microorganisms.

The culturing medium was made using seawater collected from the Oregon Coast. The seawater was, in the following order: (1) filtered using a Supor 0.2 $\mu$m filter, (2) autoclaved, (3) $CO_2$ sparged for approximately 12 hours, and (4) air sparged for approximately 24 hours. Two hepa filters and one 0.1 $\mu$m filter, in series, were used to sterilize the $CO_2$ and air.

Example 4

Detection/Quantification of Cell Growth

In order to detect cell growth, an aliquot (200 $\mu$l) of culture was taken from each well of the microtiter plate and placed in a vacuum filtration manifold device (see FIG. 1) fitted with a rectangular (48×60 mm) polycarbonate membrane, pore size 0.2 $\mu$m. The manifold and membrane were rinsed with 0.2 $\mu$m Nanopure water. The 200 $\mu$l of culture was then added to the manifold and the liquid was removed by vacuum suction. The cells were then DAPI stained, leaving the stained cells on the surface of the polycarbonate filter in the form of an array.

In certain experiments, cell growth was detected by direct microscopic examination of cells on the primary filter material. A glass slide large enough to fit the filter membrane was coated with a thin layer of immersion oil, and the arrayed membrane was laid on top. Several drops of immersion oil were laid on the membrane and a cover slip was laid on top; this "sandwich" was gently pressed together. The array was examined through a 100× oil immersion objective, using a DAPI filter set on a fluorescent microscope (Zeiss or Leica DMRB). Cells were detected based on fluorescence caused by intercalation of the dye DAPI (4',6 diamidino-2-phenylindole) into DNA. The number of cells in each spot of the array was counted, and this number was correlated with the culture sample. Typically, the sectors of an array contained 100 to 10,000 cells, although in some cases only a few (but usually >10) cells might be counted.

In other experiments, cells were transferred from the primary filter array to a secondary array material before they were examined. The polycarbonate membrane with the primary cell array was placed cell-side down onto an ultra-clean glass microslide that had been previously treated with 3-Aminopropyltriethoxysilane. The membrane was pressed onto the slide with a rubber brayer, clamped into place, and incubated at 37° C. for approximately one hour. After incubation, the membrane was peeled off leaving the cells attached to the microslide (secondary array), with transfer efficiencies approaching 100%. Transfer efficiencies were confirmed by Poisson statistics. The cell array on the glass slide can be analyzed using standard epifluorescence microscopy or laser scanning microscopy, for instance.

In general, if a culture showed a minimum of 100 cells/mL upon direct microscopic examination (as described above), it was further analyzed.

Example 5

Identification of Growing Cell Cultures Using PCR
Preparation of Nucleic Acid Samples:

This example provides a method for preparing concentrated nucleic acid samples suitable for use in amplification reactions, using dilute microbial cultures as the source of the nucleic acids. In overview, the cells are first concentrated in a centrifugation concentrator fitted with a 10,000 molecular weight ultra-filtration membrane. The cells are then lysed by the addition of lysis buffer, which is allowed to site with the cells for some time, for instance at least about 5 minutes, though the incubation time may be as much as about 120 minutes, or more. The lysis buffer is then rinsed with multiple rinses of water and the cell material, containing accessible nucleic acid molecules, is collected from the concentrator.

Vivaspin™ Concentration

A 200 µl aliquot of each culture was previously taken from the culturing wells, placed in a 5 minute UV irradiated microcentrifuge tube, and frozen at −20° C. or −80° C., depending on the expected length of storage. Cell cultures for use within one week were usually stored at −20° C.; −80° C. was used for longer term preservation. One 200 µl aliquot is sufficient for preparation of nucleic acids for further analysis.

To prepare the frozen dilution cultures for lysis and concentration, the tubes were placed into a 95° C. heat block for five minutes, then put in −80° C. for 15 minutes. This process, which helps unsure cell lysis, was repeated once, and the tubes finally thawed at room temperature.

Each 10K 0.5 ml Vivaspin centrifugation concentrator (Product No. VSO102; Vivascience, Sartorius Corporation, USA) was UV irradiated using a General Electric germicidal lamp Model No. G15T8. The concentrator tubes were set upright in a rack with lids open at a distance of 3 to 7 cm over the length of the tube for seven minutes to remove contaminating nucleic acids.

A 100 µl aliquot of autoclaved, UV irradiated Nanopure (Barnstead/Thermolyne, Dubuque, Iowa) water was placed into the Vivaspin concentrator, and let sit for one minute to one hour in order to pre-wet the concentrator. The 200 µl prepared culture was then transferred into the Vivaspin concentrator with the Nanopure water, and the column was spun at 6900 g (10K rpm in a Taylor 1624VS or Hermle Z 233 M benchtop micro-centrifuge) for six minutes, or until <20 µl of liquid remained in the concentrator.

To lyse the concentrated cells, 150 µl of UV irradiated GES lysis buffer (SM Guanidine thiocyanate, 100 mM EDTA and 0.5% Sarkosyl) was added to the concentrator, and incubated at room temperature for 25 minutes. The GES lysis buffer was removed by spinning the column at least 10 minutes at 6900 g (10K rpm in a Taylor 1624VS or Hermle Z 233 M benchtop micro-centrifuge), until <20 µl of liquid remained in the column. The column was rinsed three times with 200 µl autoclaved, UV irradiated, Nanopure water, spinning each time at 6900 g until 20–50 µl was left in the tube between rinses. Each rinse spin took about 20–40 minutes.

The lysed cell material was rinsed a final time with 100 µl autoclaved, UV irradiated, Nanopure water, and the sample concentrated by spinning at 6900 g until about 20–50 µl remained. This concentrated sample was removed from the concentrator column with a gamma irradiated barrier gel tip into a five minute-UV irradiated microcentrifuge tube, and frozen for PCR or other analysis.

Analysis of Nucleic Acid Samples

This example provides a method useful for identifying growth of organisms in very dilute culture through nucleic acid amplification.

Nucleic Acid Amplification

An initial 20 µl PCR reaction was performed using 1 µl of the concentrated liquid collected from the concentrator. A second 60–100 µl PCR was done using 1 µl from the previous PCR amplification reaction. A total of 25–33 cycles was run for each PCR, for a total of 50–66 cycles of amplification for each sample.

The PCR cocktail minus the Taq polymerase was made in batches to last 2–6 months. The final PCR reaction mix for both reactions contained 0.5 U Taq, 5% acetamide, 1.5 mM $Mg^{2-}$, 50 nM of each primer, 220 µM dNTP and 1× Taq buffer. The amplification conditions for both PCR reactions were as follows: denaturation at 94° C. for 30 seconds; hybridization at 50–55° C. (depending on primers used) for one minute; and elongation at 72° C. for two minutes.

Eubacterial or universal small subunit rRNA primers were used to prime all amplification reactions. Examples of such primers include:

```
SEQ ID NO:1 (also known as 27F):    AGR GTT TGA TCM TGG CTC AG;

SEQ ID NO:2 (also known as 68F):    TNA NAC ATG CAA GTC GAR CG;

SEQ ID NO:3 (also known as 338F):   ACT CCT ACG GGA GGC AGC;

SEQ ID NO:4 (also known as 338R):   GCT GCC TCC CGT AGG AGT;
```

-continued

SEQ ID NO:5 (also known as 519F):  CAG CMG CCG CGG TAA TWC;

SEQ ID NO:6 (also known as 519R):  GWA TTA CCG CGG CKG CTG;

SEQ ID NO:7 (also known as 1406R): ACG GGC GGT GTG TRC;

SEQ ID NO:8 (also known as 1492R): GGT TAC CTT GTT ACG ACT T; and

SEQ ID NO:9 (also known as 1521R): AAG GAG GTG ATC CAN CCR CA.

The sequences designated "F" primers (SEQ ID NOs: 1–3 and 5) are all forward (upstream) primers; those designated as "R" primers (SEQ ID NOs: 4 and 6–9) are reverse (downstream) primers. Various combinations are possible depending on the specific application.

For the PCR positive controls, a dilution series of the DNA gene of interest is useful. By way of example, $10^8$, 2000, 200, 100 and 20 copies of the 16S rRNA gene can be used as positive controls. Appropriate primers for such amplification include, but are in no way limited to, those shown in SEQ ID NOs: 1–9. Control samples show very consistent and concentrated PCR product from as few as 20 copies of a template molecule. Likewise, negative control samples (containing no DNA template) should be run with all PCR reactions. By way of example, three replicates of each negative control should be run in each PCR experiment; results were discarded if any of the negative controls showed amplification, as this was indicative of contamination in the system. The negative controls that are run in the first amplification reaction are carried over into the second reaction, and thus treated essentially like the test samples.

PCR reactions were analyzed by separation on a 1% agarose gel. Positive samples showed a strong amplification band at a size appropriate for the primers used.

Example 6

Identification of Novel Organisms
Sequencing of Amplified Nucleic Acid Molecules This example provides one method for identifying organisms grown using the described high-throughput culturing methods. Target nucleic acid molecules amplified from the cultured organisms can be sequenced, using known techniques, and the resultant sequences compared to known sequences of the target gene from known organisms. The sequences then can be placed in a phylogenetic tree, to establish the relatedness of the isolated organism to known and/or previously cultured microbial species.

Using the techniques described herein, novel organisms related to OM43, SAR11 and SAR92 have been cultured, at least for short periods of time.

Example 7

FISH Analysis of Microorganisms

Fluorescence in situ hybridization (FISH) can also be used to analyze and identify microorganisms cultured and/or isolated using the techniques described herein. This example provides one specific method for performing such FISH analysis.

Bacterial cells are incubated with oligonucleotide probes that have fluorescent labels attached, according to Glockner et al. (*Sys. Appl. Microb.* 19: 403–406, 1996). In short, the hybridization reaction takes place at elevated temperature, usually 42° C., for at least 90 minutes, in a hybridization solution of 0.9 M NaCl, 20 mM Tris/HCl pH 7.4, 35% formamide and 0.01% SDS. Fluorescent oligonucleotide probes are added at a final reaction concentration of 2 ng/µl. After hybridization, the cells are washed in two successive hot washes, usually 42° C., in a wash solution of 70 mM NaCl, 20 mM Tris/HCl pH 7.4, 5 mM EDTA and 0.01% SDS. The cells are subsequently counterstained with DAPI at a final reaction concentration of 5 ug/ml. Cell staining can then be detected using microscopy or other detection systems.

This invention provides methods for high-throughput culturing and identification of novel microorganisms from natural environments. The invention further provides methods for determining positive and/or negative interactions between microorganisms, including production of antibiotics or other chemical compounds. It will be apparent that precise details of the methods described may be varied or modified without departing from the spirit of the described invention. We claim all such modifications and variations that fall within the scope and spirit of the claims below.

We claim:

1. A method of isolating and identifying a microbial species from a source environment, comprising:

gathering from the source environment a sample suspected of containing a microorganism;

providing a volume of culture medium to the sample in at least one microtiter plate compartment in order to dilute the sample to a culture density of 1 to 10 cells per milliliter, wherein the culture medium comprises substrate concentrations that are similar to those of the source environment;

incubating the microorganism in the culture medium for a period of time and in an environment sufficient to result in growth of the microorganism if the culture medium and environment are capable of supporting such growth to produce a culture sample;

detecting growth of the microorganism using an automated detection method that comprises removing a portion of the culture sample and depositing the portion onto a surface, wherein detecting growth of the microorganism consists of detecting an increase in a number of microorganisms in the compartment to no more than about $5 \times 10^4$ cells/milliliter, and wherein detecting growth of the microorganism indicates that the microbial species has been isolated from the source environment; and identifying the microbial species, wherein identifying the microorganism comprises hybridization of a probe to a nucleic acid molecule of the microorganism; amplification of a nucleic acid molecule of the microorganism; immunodetection of a molecule of the microorganism; sequencing of a nucleic acid molecule of the microorganism; or a combination of two or more thereof.

2. The method of claim 1, wherein a plurality of individual microorganisms are separately incubated in microtiter plate compartments.

3. The method of claim 2, wherein the plurality is at least 20.

4. The method of claim 2, wherein the plurality is at least 50.

5. The method of claim 2, wherein the plurality is at least 100.

6. The method of claim 2, wherein the plurality is at least 400.

7. The method of claim 2, wherein the plurality is at least 1000.

8. The method of claim 2, wherein the plurality is at least 1500.

9. The method of claim 1, wherein the source environment is a non-laboratory environment.

10. The method of claim 1, wherein the source environment is a natural environment.

11. The method of claim 1, wherein more than one microorganism is gathered from the source environment.

12. The method of claim 11, wherein each organism is provided a volume of medium in a separate compartment.

13. The method of claim 12, wherein the volume of medium is no greater than about 1 m/l.

14. The method of claim 12, wherein the organisms are placed in the separate compartments using flow cytometry, cell sorting, or dilution.

15. The method of claim 1, further comprising counting at least one microorganism that grew.

16. The method of claim 1, wherein identifying the microorganism includes hybridization of a probe to a nucleic acid molecule of the microorganism.

17. The method of claim 1, wherein identifying the microorganism includes amplification of a nucleic acid molecule of the microorganism.

18. The method of claim 1, wherein identifying the microorganism includes immunodetection of a molecule of the microorganism.

19. The method of claim 1, wherein identifying the microorganism includes sequencing of a nucleic acid molecule of the microorganism.

20. The method of claim 1, wherein identification of the microorganism is automated.

21. The method of claim 15, wherein identifying or counting a microorganism comprises depositing cells in a two-dimensional array, such that different cultures arising from different cells each occupy a unique position in the array.

22. The method of claim 15, wherein identifying or counting a microorganism comprises use of a technique that reveals a genetic or enzymatic property of the microorganisms.

23. The method of claim 15, wherein a cultured strain of bacteria, called a reporter strain, is added to the medium with an unknown cell from nature, such that production of at least one compound by the unknown cell is revealed by a growth or genetic responses of the reporter strain.

24. The method of claim 1, wherein the detection method comprises removal of substantially all of the medium from the cultured sample.

25. The method of claim 1, wherein identifying the at least one microbial species comprises sequencing a target nucleic acid sequence of the microbial species, and comparing the sequence of the target nucleic acid to at least one known sequence of the target nucleic acid from at least one known organism.

26. The method of claim 25, wherein the target nucleic acid sequence is a ribosomal RNA sequence.

27. A method of isolating and identifying a microbial species from a marine source environment, comprising:
  gathering from the source environment a sample suspected of containing a plurality of microorganisms;
  providing a volume of culture medium based on sea water to the plurality of microorganisms in a plurality of microtiter plate compartments, in order to dilute the sample such that each compartment receives no more than about three microorganisms;
  incubating the plurality of microorganisms in the medium for a period of time and in an environment sufficient to result in growth of the microorganism if the medium and environment are capable of supporting such growth to produce a plurality of culture samples;
  detecting growth of at least one of the plurality of microorganisms using a detect method that comprises depositing a portion of the culture sample onto a surface using a filtration manifold, wherein detecting growth of the microorganism comprises an increase in the number of microorganisms in the compartment to no more than about $5 \times 10^4$ cells/milliliter, and wherein detecting growth of the at least one microorganism indicates that the microbial species has been isolated from the source environment; and
  identifying the microbial species, using a method that comprises:
    sequencing a ribosomal RNA sequence of the microbial species;
    comparing the sequence of the ribosomal RNA to at least one known ribosomal RNA sequence from at least one known organism; and
    assigning an identity to the microbial species based on sequence similarity to the ribosomal RNA of the known organism.

28. The method of claim 1, wherein the sample gathered from the source environment contains at least about 5 microorganisms.

29. The method of claim 1, wherein the sample gathered from the source environment contains at least about 10 microorganisms.

30. The method of claim 1, wherein the sample gathered from the source environment contains at least about 20 microorganisms.

* * * * *

UNITED STATES PATENT AND TRADEMARK OFFICE
CERTIFICATE OF CORRECTION

PATENT NO. : 6,951,714 B2  Page 1 of 1
APPLICATION NO. : 10/053243
DATED : October 4, 2005
INVENTOR(S) : Giovannoni et al.

It is certified that error appears in the above-identified patent and that said Letters Patent is hereby corrected as shown below:

On the Cover:

In Other Publications, "High-Affinity. Novel" should be --High-Affinity, Novel--.

In the Specification:

Column 1, line 58, "DeLong *Proc.*" should be --DeLong, *Proc.*--.

Column 2, line 15, "*Limnol, Oceanog.*" should be --*Limnol. Oceanogr.*--.

Column 2, line 48, "Hioms et al.," should be --Hiorns et al.,--.

Column 2, line 49, "*Oceanog.*" should be --*Oceanogr.*--.

Column 7, line 35, "within the at least the two" should be --within at least the two--.

Column 8, line 45, "general be correlated the size" should be --general be correlated to the size--.

Column 13, line 37, "Dyhrrnan" should be --Dyhrman--.

Column 17, line 54, "which helps unsure cell lysis" should be --which helps insure cell lysis--.

Column 17, line 57, "(Product No. VSO102" should be --(Product No. VS0102--.

Column 18, line 17, "(SM" should be --(5M--.

Column 18, line 50, "1.5 mM $Mg^{2-}$" should be --1.5mM $Mg^{2+}$--.

Signed and Sealed this

Twenty-fourth Day of June, 2008

JON W. DUDAS
*Director of the United States Patent and Trademark Office*